United States Patent
Zhang et al.

(10) Patent No.: US 10,943,673 B2
(45) Date of Patent: Mar. 9, 2021

(54) METHOD AND APPARATUS FOR MEDICAL DATA AUTO COLLECTION SEGMENTATION AND ANALYSIS PLATFORM

(71) Applicant: TENCENT AMERICA LLC, Palo Alto, CA (US)

(72) Inventors: Shangqing Zhang, Palo Alto, CA (US); Min Tu, Cupertino, CA (US); Nan Du, Santa Clara, CA (US); Yusheng Xie, Mountain View, CA (US); Yaliang Li, Santa Clara, CA (US); Tao Yang, Mountain View, CA (US); Wei Fan, New York, NY (US)

(73) Assignee: TENCENT AMERICA LLC, Palo Alto, CA (US)

( * ) Notice: Subject to any disclaimer, the term of this patent is extended or adjusted under 35 U.S.C. 154(b) by 134 days.

(21) Appl. No.: 16/379,992

(22) Filed: Apr. 10, 2019

(65) Prior Publication Data
US 2020/0327964 A1    Oct. 15, 2020

(51) Int. Cl.
G06F 16/30    (2019.01)
G16H 10/00   (2018.01)
G06F 16/35    (2019.01)
G06F 16/31    (2019.01)

(52) U.S. Cl.
CPC ............ *G16H 10/00* (2018.01); *G06F 16/31* (2019.01); *G06F 16/35* (2019.01)

(58) Field of Classification Search
CPC .......... G06F 16/31; G06F 16/35; G16H 10/00
See application file for complete search history.

(56) References Cited

U.S. PATENT DOCUMENTS

| 2004/0225865 A1* | 11/2004 | Cox ................... G06F 16/2455 712/34 |
| 2012/0209847 A1 | 8/2012 | Rangan |
| 2013/0046558 A1 | 2/2013 | Landi et al. |

(Continued)

FOREIGN PATENT DOCUMENTS

| CN | 109299239 A | * 2/2019 |
| WO | 2007/131064 A2 | 11/2007 |

OTHER PUBLICATIONS

Article entitled "Evaluation of Clinical Text Segmentation to Facilitate Cohort Retrieval", by Edinger et al., dated Apr. 16, 2018.*

(Continued)

*Primary Examiner* — Mahesh H Dwivedi
(74) *Attorney, Agent, or Firm* — Sughrue Mion, PLLC

(57) ABSTRACT

A method of medical data auto collection segmentation and analysis, includes collecting, from a plurality of sources, unstructured medical data in a plurality of formats, recognizing a medical name entity of each piece of the unstructured medical data, using a medical dictionary, and performing semantic text segmentation on each piece of the unstructured medical data so that each piece of the unstructured medical data is partitioned into groups sharing a same topic. The method further includes generating, as structured medical data, each piece of the unstructured medical data of which the medical name entity is recognized, each piece of the unstructured medical data being partitioned into the groups, and indexing the structured medical data into elastic search clusters.

17 Claims, 7 Drawing Sheets

(56) References Cited

U.S. PATENT DOCUMENTS

| | | | |
|---|---|---|---|
| 2015/0046190 A1 | 2/2015 | Strongwater | |
| 2017/0286529 A1* | 10/2017 | O'Neill | G06F 40/279 |
| 2018/0189387 A1* | 7/2018 | Kim | G06F 16/35 |
| 2019/0013093 A1* | 1/2019 | Slepian | G06F 40/10 |
| 2019/0074072 A1 | 3/2019 | Aldridge et al. | |
| 2020/0065374 A1* | 2/2020 | Gao | G06N 3/084 |
| 2020/0134024 A1* | 4/2020 | Banisakher | G16H 15/00 |
| 2020/0134511 A1* | 4/2020 | Ho | G06F 16/94 |
| 2020/0233875 A1* | 7/2020 | Penev | G06F 40/295 |

OTHER PUBLICATIONS

Article entitled "Clinical Named Entity Recognition from Chinese Electronic Health Records via Machine Learning Methods", by Xu et al., dated Dec. 17, 2017.*

Article entitled "Data Processing and Text Mining Technologies on Electronic Medical Records: A Review", by Sun et al., dated 2018.*

Article entitled "Topic Segmentation and Medical Named Entities Recognition for Pictorially Visualizing Health Record Summary System", by Ruan, dated Apr. 3, 2019.*

Article entitled "Keyword extraction and structuralization of medical reports", by Tsai et al., dated 2019.*

Xu et al., "Data-Driven Information Extraction from Chinese Electric Medical Records", PLOS ONE, Aug. 21, 2015, [Internet] <https://www.ncbi.nlm.nih.gov/pmc/articles/PMC4546596/pdf/pone.0136270.pdf>, pp. 1-18 (total 18 pages).

International Search report for PCT/US2020/020068 dated May 27, 2020.

Written Opinion of the International Searching Authority for PCT/US2020/020068 dated May 27, 2020.

\* cited by examiner

METHOD AND APPARATUS FOR MEDICAL DATA AUTO COLLECTION SEGMENTATION AND ANALYSIS PLATFORM

BACKGROUND

Traditional medical data platforms are very costly and inefficient. A first approach is using standard or structured medical books for a dataset, which are neither easy nor cheap to obtain access to. A second approach is asking a professional person with a medical background to get involved in the process and to perform labelling or data cleaning. However, this approach leads to an unpredictable processing time, as well as a high cost on manual labor work.

Another disadvantage of the current approaches is that a volume of data might be efficient for a human to understand, but not enough for a machine to learn. In fact, most of deep learning-based methods require a large amount of training data to learn a model.

SUMMARY

According to embodiments, a method of medical data auto collection segmentation and analysis, includes collecting, from a plurality of sources, unstructured medical data in a plurality of formats, recognizing a medical name entity of each piece of the unstructured medical data, using a medical dictionary, and performing semantic text segmentation on each piece of the unstructured medical data so that each piece of the unstructured medical data is partitioned into groups sharing a same topic. The method further includes generating, as structured medical data, each piece of the unstructured medical data of which the medical name entity is recognized, each piece of the unstructured medical data being partitioned into the groups, and indexing the structured medical data into elastic search clusters.

According to embodiments, an apparatus for medical data auto collection segmentation and analysis, includes at least one memory configured to store program code, and at least one processor configured to read the program code and operate as instructed by the program code. The program code includes collecting code configured to cause the at least one processor to collect, from a plurality of sources, unstructured medical data in a plurality of formats, recognizing code configured to cause the at least one processor to recognize a medical name entity of each piece of the unstructured medical data, using a medical dictionary, and performing code configured to cause the at least one processor to perform semantic text segmentation on each piece of the unstructured medical data so that each piece of the unstructured medical data is partitioned into groups sharing a same topic. The program code further includes first generating code configured to cause the at least one processor to generate, as structured medical data, each piece of the unstructured medical data of which the medical name entity is recognized, each piece of the unstructured medical data being partitioned into the groups, and indexing code configured to cause the at least one processor to index the structured medical data into elastic search clusters.

According to embodiments, a non-transitory computer-readable medium storing instructions that, when executed by at least one processor of a device, cause the at least one processor to collect, from a plurality of sources, unstructured medical data in a plurality of formats, recognize a medical name entity of each piece of the unstructured medical data, using a medical dictionary, perform semantic text segmentation on each piece of the unstructured medical data so that each piece of the unstructured medical data is partitioned into groups sharing a same topic, generate, as structured medical data, each piece of the unstructured medical data of which the medical name entity is recognized, each piece of the unstructured medical data being partitioned into the groups, and index the structured medical data into elastic search clusters.

DETAILED DESCRIPTION

Figure 1:
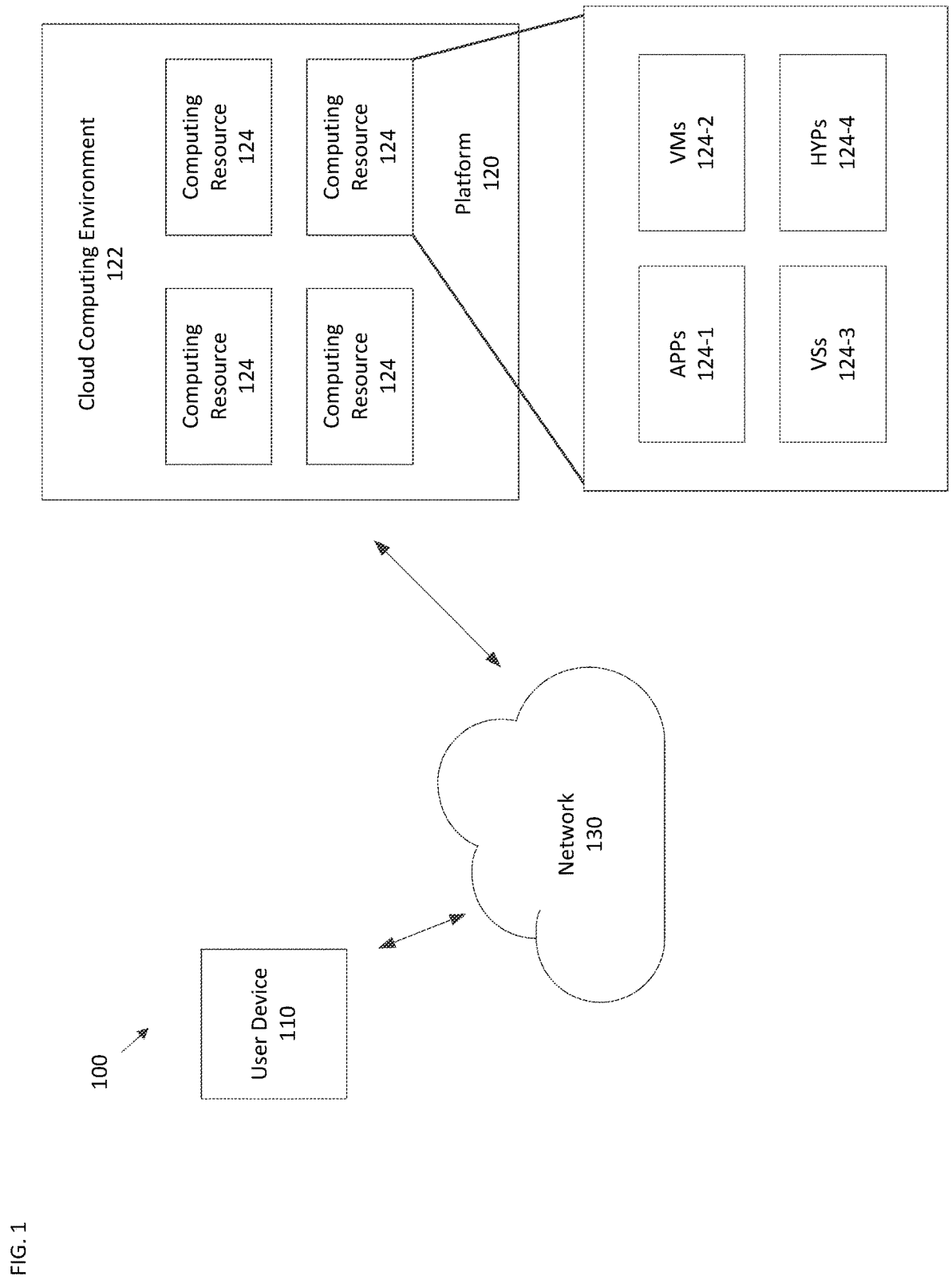
FIG. 1 is a diagram of an environment in which methods, apparatuses and systems described herein may be implemented, according to embodiments.

Embodiments described herein include a medical data platform that builds a high-quality and reliable medical knowledge base with a low cost on data collection and transforming. The medical data platform is an auto-scaled, large data driven, elastic search-based platform that builds a high-quality medical facts storage from a large amount of low-quality, low-cost and unsupervised data. Main components of the platform include: web crawlers for raw data collection, an extract, transform, load (ETL) pipeline for optical character recognition (OCR) and data cleaning and formatting, latent Dirichlet allocation (LDA) and non-negative matrix factorization (NMF) models for text segmentation, and an auto-scaled elastic search cluster for data indexing and storage.

In detail, because a requirement of utilizing deep learning models for solving medical problems keeps increasing, a solid and decent medical facts and data storage is used. Thus, the medical data platform collects a large amount of low-quality, high-noised data from medical forums, medical websites and scientific magazines, filtering out real medical cases, diagnosis, articles, papers and books. This multi-sources, unstructured data is placed into ETL pipelines that use natural language processing (NLP) components for entity recognition and normalization to turn the unstructured data into structured entities. For large texts and documentation, the medical data platform performs a combined topic modeling on the structured entities, using NMF and LDA models for semantic text segmentation, to find and enforce internal relations between the structured entities. To solve a problem of high volume data storage and efficiency, the medical data platform uses an elastic search cluster to achieve an auto scaling, distributed storage system.

The medical data platform above addresses all disadvantages from traditional data platforms. For example, to solve a data volume and cost problem, the medical data platform uses web crawlers to grab millions of free documents, paragraphs and conversations from medical clinic-related websites, and to inject such multi-sources supported data into a transforming pipeline to turn the data into a structured data format.

In another example, to guarantee data accuracy and high-quality, the medical platform uses NLP word embedding models to recognize medical-related entities with different categories, and write these entities into an elastic search cluster for indexing. An elastic search uses term frequency-inverse document frequency (tf-idf) and Best Matching 25 (BM25) score mechanisms for a data search. This method greatly reduces noisy data coming from a large data volume, and increases a quality and an accuracy for only topics or domains of interest.

In still another example, to make the medical data platform easy and useful for deep learning purposes, an easy-to-use interface is needed. The medical data platform uses a RESTful application program interface (API) interface to search for a medical dataset. This makes the medical data platform easy to be plugged into a popular machine learning framework like TensorFlow.

FIG. 1 is a diagram of an environment 100 in which methods, apparatuses and systems described herein may be implemented, according to embodiments. As shown in FIG. 1, environment 100 may include a user device 110, a platform 120, and a network 130. Devices of environment 100 may interconnect via wired connections, wireless connections, or a combination of wired and wireless connections.

User device 110 includes one or more devices capable of receiving, generating, storing, processing, and/or providing information associated with platform 120. For example, user device 110 may include a computing device (e.g., a desktop computer, a laptop computer, a tablet computer, a handheld computer, a smart speaker, a server, etc.), a mobile phone (e.g., a smart phone, a radiotelephone, etc.), a wearable device (e.g., a pair of smart glasses or a smart watch), or a similar device. In some implementations, user device 110 may receive information from and/or transmit information to platform 120.

Platform 120 includes one or more devices as described elsewhere herein. In some implementations, platform 120 may include a cloud server or a group of cloud servers. In some implementations, platform 120 may be designed to be modular such that software components may be swapped in or out depending on a particular need. As such, platform 120 may be easily and/or quickly reconfigured for different uses.

In some implementations, as shown, platform 120 may be hosted in cloud computing environment 122. Notably, while implementations described herein describe platform 120 as being hosted in cloud computing environment 122, in some implementations, platform 120 is not be cloud-based (i.e., may be implemented outside of a cloud computing environment) or may be partially cloud-based.

Cloud computing environment 122 includes an environment that hosts platform 120. Cloud computing environment 122 may provide computation, software, data access, storage, etc. services that do not require end-user (e.g., user device 110) knowledge of a physical location and configuration of system(s) and/or device(s) that hosts platform 120. As shown, cloud computing environment 122 may include a group of computing resources 124 (referred to collectively as "computing resources 124" and individually as "computing resource 124").

Computing resource 124 includes one or more personal computers, workstation computers, server devices, or other types of computation and/or communication devices. In some implementations, computing resource 124 may host platform 120. The cloud resources may include compute instances executing in computing resource 124, storage devices provided in computing resource 124, data transfer devices provided by computing resource 124, etc. In some implementations, computing resource 124 may communicate with other computing resources 124 via wired connections, wireless connections, or a combination of wired and wireless connections.

As further shown in FIG. 1, computing resource 124 includes a group of cloud resources, such as one or more applications ("APPs") 124-1, one or more virtual machines ("VMs") 124-2, virtualized storage ("VSs") 124-3, one or more hypervisors ("HYPs") 124-4, or the like.

Application 124-1 includes one or more software applications that may be provided to or accessed by user device 110 and/or platform 120. Application 124-1 may eliminate a need to install and execute the software applications on user device 110. For example, application 124-1 may include software associated with platform 120 and/or any other software capable of being provided via cloud computing environment 122. In some implementations, one application 124-1 may send/receive information to/from one or more other applications 124-1, via virtual machine 124-2.

Virtual machine 124-2 includes a software implementation of a machine (e.g., a computer) that executes programs like a physical machine. Virtual machine 124-2 may be either a system virtual machine or a process virtual machine, depending upon use and degree of correspondence to any real machine by virtual machine 124-2. A system virtual machine may provide a complete system platform that supports execution of a complete operating system ("OS"). A process virtual machine may execute a single program, and may support a single process. In some implementations, virtual machine 124-2 may execute on behalf of a user (e.g., user device 110), and may manage infrastructure of cloud computing environment 122, such as data management, synchronization, or long-duration data transfers.

Virtualized storage 124-3 includes one or more storage systems and/or one or more devices that use virtualization techniques within the storage systems or devices of computing resource 124. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 124-4 may provide hardware virtualization techniques that allow multiple operating systems (e.g., "guest operating systems") to execute concurrently on a host computer, such as computing resource 124. Hypervisor 124-4 may present a virtual operating platform to the guest operating systems, and may manage the execution of the guest operating systems. Multiple instances of a variety of operating systems may share virtualized hardware resources.

Network 130 includes one or more wired and/or wireless networks. For example, network 130 may include a cellular network (e.g., a fifth generation (5G) network, a long-term evolution (LTE) network, a third generation (3G) network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, or the like, and/or a combination of these or other types of networks.

The number and arrangement of devices and networks shown in FIG. 1 are provided as an example. In practice, there may be additional devices and/or networks, fewer devices and/or networks, different devices and/or networks, or differently arranged devices and/or networks than those shown in FIG. 1. Furthermore, two or more devices shown in FIG. 1 may be implemented within a single device, or a single device shown in FIG. 1 may be implemented as multiple, distributed devices. Additionally, or alternatively, a set of devices (e.g., one or more devices) of environment 100 may perform one or more functions described as being performed by another set of devices of environment 100.

Figure 2:
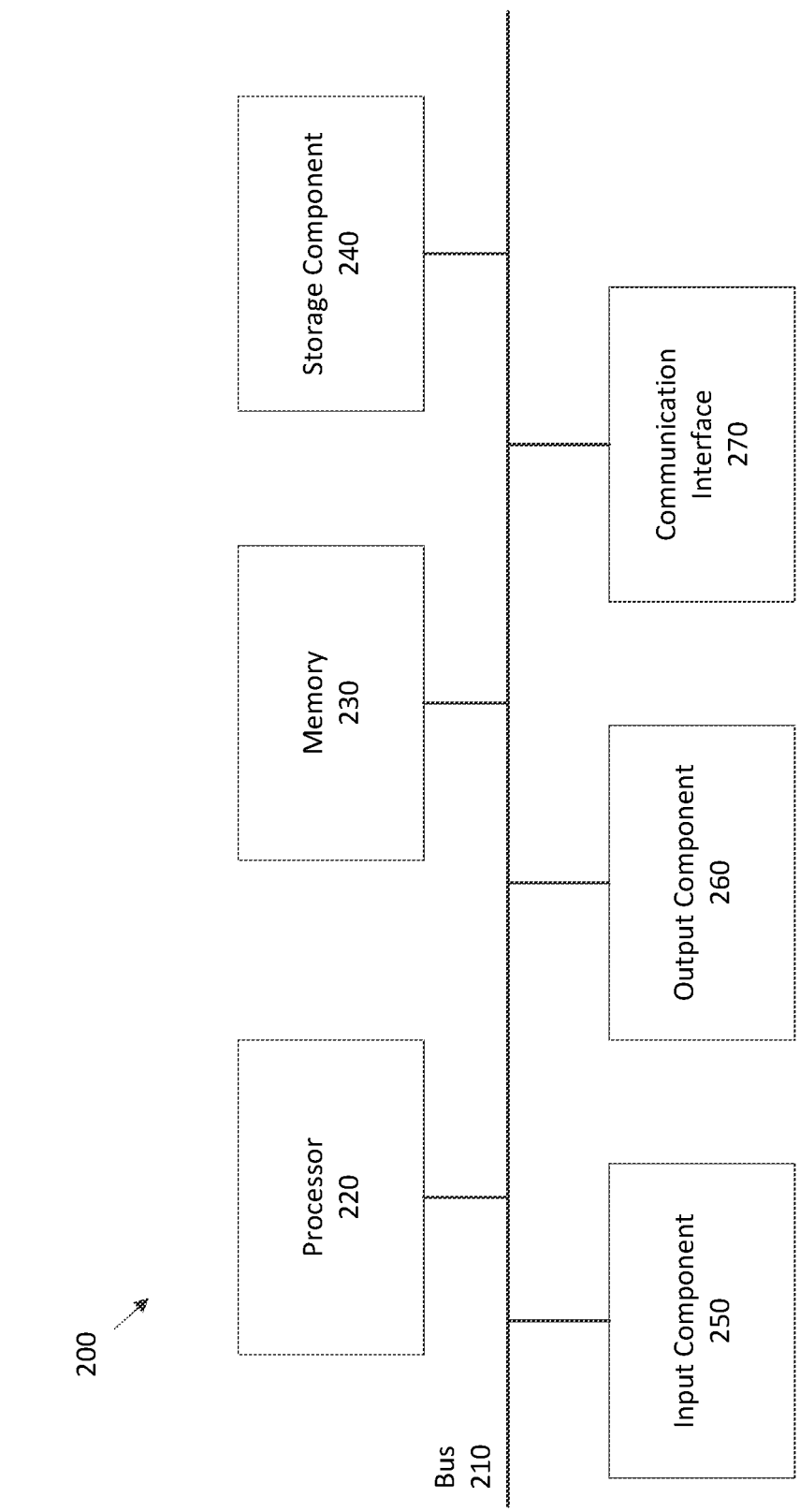
FIG. 2 is a diagram of example components of one or more devices of FIG. 1.

FIG. 2 is a diagram of example components of one or more devices of FIG. 1. A device 200 may correspond to user device 110 and/or platform 120. As shown in FIG. 2, device 200 may include a bus 210, a processor 220, a memory 230, a storage component 240, an input component 250, an output component 260, and a communication interface 270.

Bus 210 includes a component that permits communication among the components of device 200. Processor 220 is implemented in hardware, firmware, or a combination of hardware and software. Processor 220 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 220 includes one or more processors capable of being programmed to perform a function. Memory 230 includes a random access memory (RAM), a read only memory (ROM), and/or another type of dynamic or static storage device (e.g., a flash memory, a magnetic memory, and/or an optical memory) that stores information and/or instructions for use by processor 220.

Storage component 240 stores information and/or software related to the operation and use of device 200. For example, storage component 240 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 250 includes a component that permits device 200 to receive information, such as via user input (e.g., a touch screen display, a keyboard, a keypad, a mouse, a button, a switch, and/or a microphone). Additionally, or alternatively, input component 250 may include a sensor for sensing information (e.g., a global positioning system (GPS) component, an accelerometer, a gyroscope, and/or an actuator). Output component 260 includes a component that provides output information from device 200 (e.g., a display, a speaker, and/or one or more light-emitting diodes (LEDs)).

Communication interface 270 includes a transceiver-like component (e.g., a transceiver and/or a separate receiver and transmitter) that enables device 200 to communicate with other devices, such as via a wired connection, a wireless connection, or a combination of wired and wireless connections. Communication interface 270 may permit device 200 to receive information from another device and/or provide information to another device. For example, communication interface 270 may include an Ethernet interface, an optical interface, a coaxial interface, an infrared interface, a radio frequency (RF) interface, a universal serial bus (USB) interface, a Wi-Fi interface, a cellular network interface, or the like.

Device 200 may perform one or more processes described herein. Device 200 may perform these processes in response to processor 220 executing software instructions stored by a non-transitory computer-readable medium, such as memory 230 and/or storage component 240. A computer-readable medium is defined herein as a non-transitory memory device. A memory device includes memory space within a single physical storage device or memory space spread across multiple physical storage devices.

Software instructions may be read into memory 230 and/or storage component 240 from another computer-readable medium or from another device via communication interface 270. When executed, software instructions stored in memory 230 and/or storage component 240 may cause processor 220 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 2 are provided as an example. In practice, device 200 may include additional components, fewer components, different components, or differently arranged components than those shown in FIG. 2. Additionally, or alternatively, a set of components (e.g., one or more components) of device 200 may perform one or more functions described as being performed by another set of components of device 200.

Embodiments described herein establish a large-scaled, good-quality medical knowledge base without relying on an expensive and limited medical dataset as well as time-consuming manual labeling work. In detail, a medical data platform described herein utilizes a large amount of free or low-cost data that is generated by users and physicians from the Internet. By normalizing such multi-sourced, unstructured data with NLP modules in the medical data platform, and indexing all documents based on an elastic search cluster, the medical data platform provides strong correlated medical facts and data points by ranking and comparing a similarity from inputs that are provided to the medical. The medical data platform uses a RESTful API interface to more easily be embedded with popular deep learning platforms, which makes the medical data platform more powerful to utilize its large volume datasets attribute.

Figure 3:
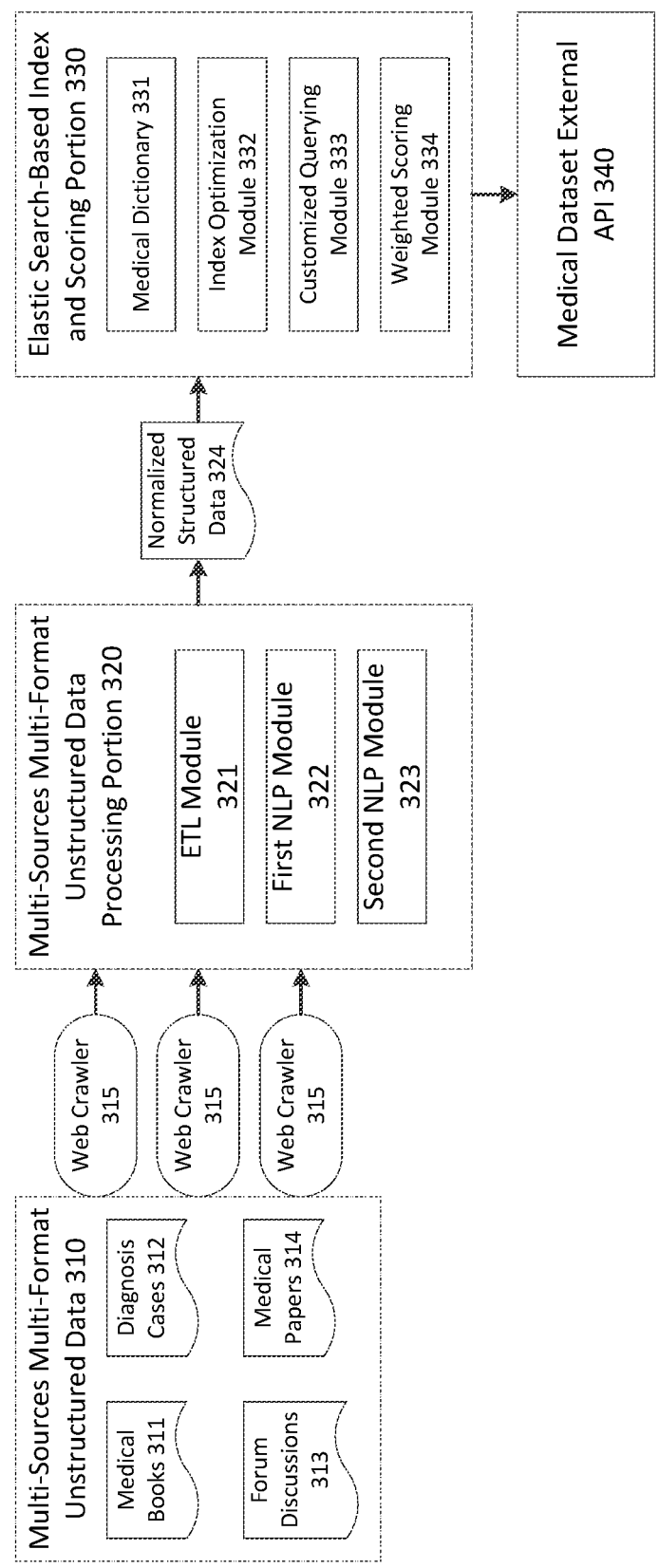
FIG. 3 is a diagram of a component architecture of a medical data platform, according to embodiments.

FIG. 3 is a diagram of a component architecture of a medical data platform 300, according to embodiments.

Referring to FIG. 3, the medical data platform 300 includes multi-sources, multi-format, unstructured data 310, web crawlers 315, a multi-sources, multi-format unstructured data processing portion 320, an elastic search-based index and scoring portion 330, and a medical dataset external API 340.

The unstructured data 310 may include, for example, medical books 311, diagnosis cases 312, forum discussions 313 and medical papers 314.

The web crawlers 315 crawl through the Internet to collect the unstructured data 310.

The processing portion 320 includes an ETL module 321, a first NLP module 322 and a second NLP module 323 that process the collected unstructured data 310 into normalized structure data 324.

The ETL module 321 performs data cleaning and formatting of the collected unstructured data 310.

The first NLP module 322 performs name entity recognition on the unstructured data 310 that may be cleaned and formatted. In detail, the medical data platform 300 may include a word embedding-based medical dictionary 331 for name entity recognition and normalization, which provides a high-quality professional medical dataset with millions of free contents that are generated from websites and forums. To utilize all of the high-noised unstructured data 310, good normalization is key. The first NLP module 322 uses a word embedding-based mechanism to learn the medical dictionary 331 from all of the raw unstructured data 310. The mechanism may include selecting, from the unstructured data 310, 128 features to represent different dimension concepts of medical entities, and using a Skip-gram model to train a word vector and topic model. After obtaining a word vector, a cosine of vectors is calculated as a similarity. A synonym dictionary, a stop-word dictionary and an entity dictionary are generated based on the word vector. After data pre-processing, each piece of contents or the unstructured data 310 is projected to vectors and mapped to a normalized medical entity. This normalization phrase greatly reduces a noise influence from the raw unstructured data 310 and reduces downstream modules of the medical data platform 300.

The second NLP module 323 performs semantic text segmentation of the unstructured data 310 that may be cleaned and formatted.

By sampling different data points collected from all online resources, the contents or the unstructured data 310 may only partially contain useful medical information. Further, sentences about the same topic may be naturally grouped together. Based on these points, it can be assumed that the further two sentences are located in a whole content, the less likely they have a correlation from a semantic perspective. Thus, a combined method is performed using an LDA model and an NMF model for topic modeling.

Figure 4:
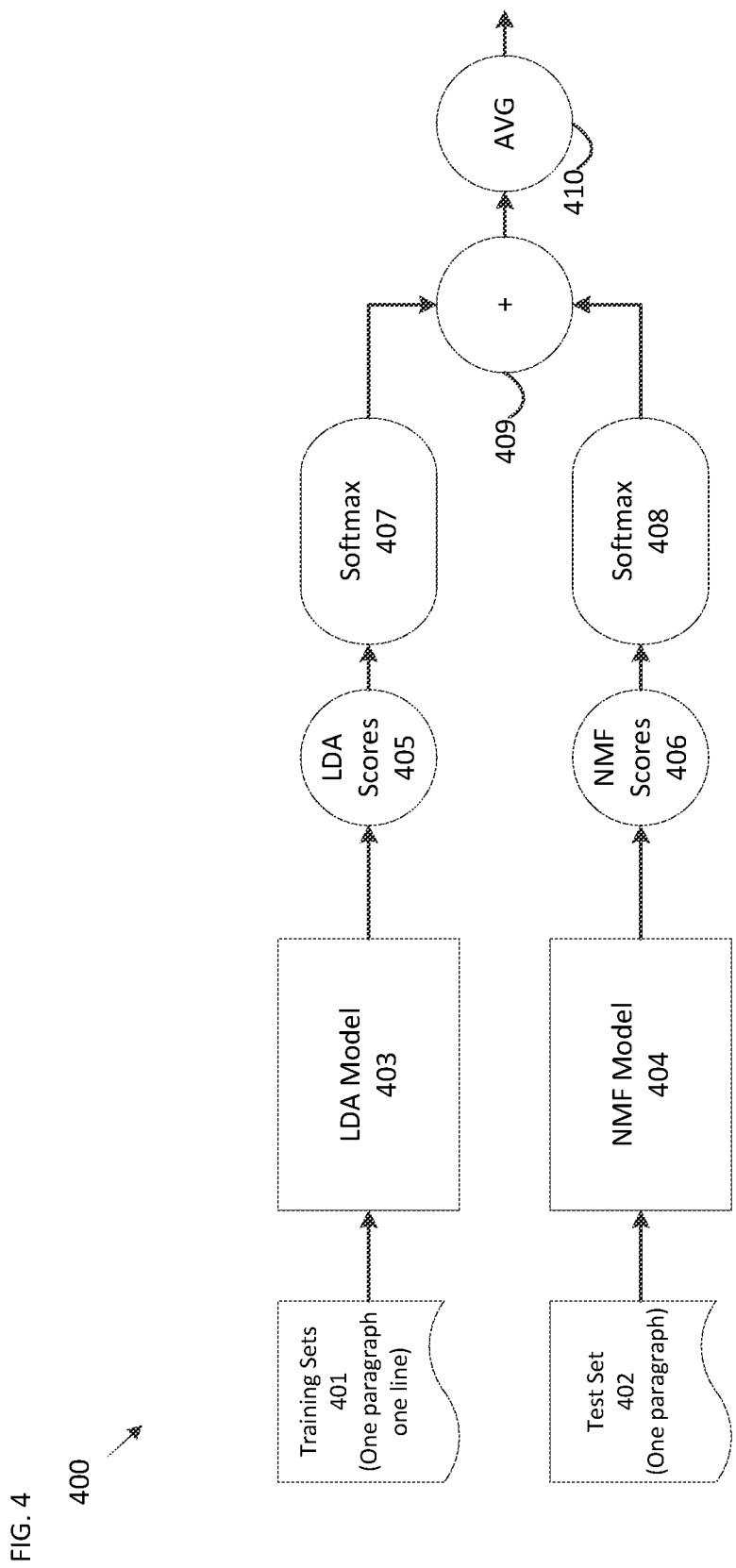
FIG. 4 is a diagram of a topic probability structure that is implemented in an NLP module that performs semantic text segmentation, according to embodiments.

FIG. 4 is a diagram of a topic probability structure 400 that is implemented in an NLP module (e.g., the second NLP module 323) that performs semantic text segmentation, according to embodiments.

The structure 400 includes an LDA model 403, an NMF model 404, a softmax function 407, a softmax function 408, a summation block 409, and an averaging block 410.

The LDA model 403 is trained by whole-word training sets 401 corresponding to the unstructured data 310. Each of the training sets 401 may be partitioned by paragraph and/or by line or sentence.

The NMF model 404 is trained by a test set 402 corresponding to the unstructured data 310. The test set 402 may be partitioned by line or sentence.

For each sentence in each paragraph of the unstructured data 310, the LDA model 403 outputs LDA scores 405, and the NMF model 404 outputs NMF scores 406. The softmax function 407 is performed on the LDA scores 405 to generate first standard derivation scores for at most 3 sentences of the sentence's neighbors in 2 directions. The softmax function 408 is performed on the NMF scores 406 to generate second standard derivation scores for at most 3 sentences of the sentence's neighbors in 2 directions.

The summation block 409 sums the first standard derivation scores and the second standard derivation scores. The averaging block 410 determines an average score by averaging the summed first standard derivation scores and the second standard derivation scores.

Referring again to FIG. 3, based on the average score, the second NLP module 323 determines a topic of the sentence. Based on the above-described topic modeling, each input paragraph is partitioned by groups of sentences sharing the same topic. An accuracy of the structured data 324 significantly increases, using semantic text segmentation compared with using sentence-only or paragraph-only partition.

The processing portion 320 outputs the normalized structure data 324. Each piece of the structured data 324 may be cleaned and formatted, correspond to a recognized medical name entity, and include paragraphs, each of which is partitioned by groups of sentences sharing the same topic.

The elastic search-based index and scoring portion 330 indexes and scores the structured data 324 into elastic search clusters for storing and output or display via the medical dataset external API 340. The API 340 may be used to search for at least one of the elastic search clusters, and display the at least one of the elastic search clusters as a medical dataset.

The elastic search-based index and scoring portion 330 may include the medical dictionary 331 and an index optimization module 332 that performs tree structure indexing on the structured data 324 to write the structured data 324 into the elastic search clusters. In detail, humans have a natural preference to group contents to represent their semantic information or hieratical structure. In different raw data sources (i.e., the multi-sources, multi-format unstructured data 310), many useful hieratic medical information could be found for metadata of a raw data point. For example, an online discussion about a patient describing his own clinical symptoms may be categorized or tagged by physicians or a website. Such pre-labeled work may be very valuable for increasing data quality for the medical data platform 300. Thus, key entities from metadata is marked out from the unstructured data 310 or the structured data 324, and a tree structure is reconstructed using the key entities, for the unstructured data 310 or the structured data 324. That is, the hieratical medical information of the unstructured data 310 or the structured data 324 is kept and injected into an elastic search cluster. Important layers or relationships may thus be indexed accordingly and be given different weights. Comparing a flat injection of elastic search clustering with using a tree-structure index for elastic search clustering. by highlighting an inner relationship and hieratical information, data quality is increased.

Figure 5:
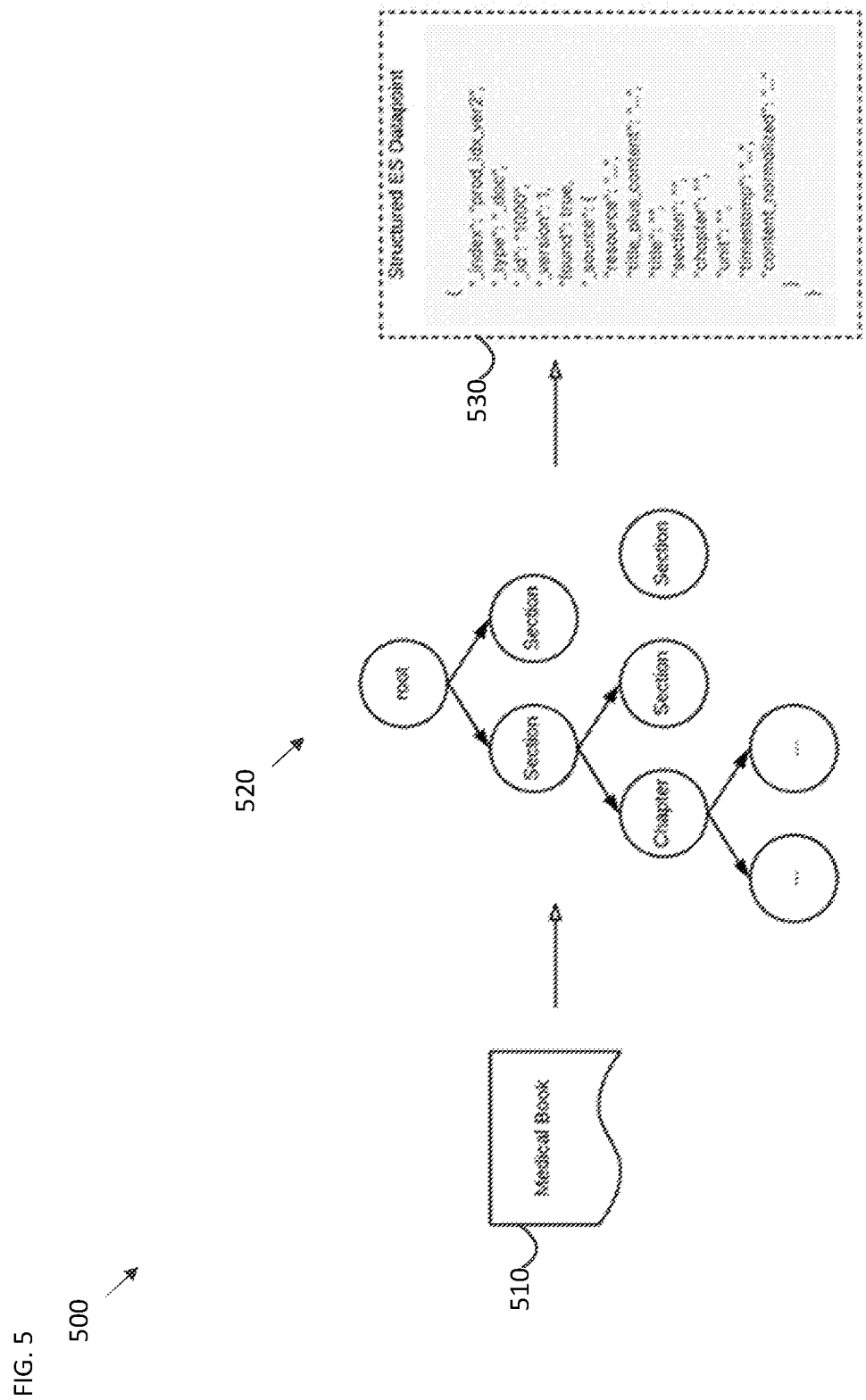
FIG. 5 is a diagram of a method of generating an elastic search cluster, using a semantic hieratical structure from data, according to embodiments.

FIG. 5 is a diagram of a method of generating an elastic search cluster, using a semantic hieratical structure from data, according to embodiments.

Referring to FIG. 5, for example, hieratical medical information is extracted from a medical book 510 and used to generate a tree structure 520 including a root node and leaf nodes, e.g., "Section" and "Chapter." The tree structure 520 is used to generate an elastic search cluster or a structured elastic search (ES) datapoint 530.

Referring again to FIG. 3, the elastic search-based index and scoring portion 330 may further include a customized querying module 333 that customizes querying for the elastic search clusters, and a weight scoring module 334 that applies the different weights respectively to the elastic search clusters.

In experiments testing a quality and an accuracy of a medical dataset or an elastic search cluster of the medical data platform 300, 12,000 real and difficult medical questions from China National Medical Licensing Examination were input into the medical data platform 300. Each question has five choices, only one choice is the right answer, and 20% is a random guess correction rate. The medical data platform 300 was used to make a brute-forced query by only combining each choice with a question, without using any deep learning model. A top 1 accuracy rate significantly increased to 43%, and a top 2 accuracy rate is 63%.

Figure 6:
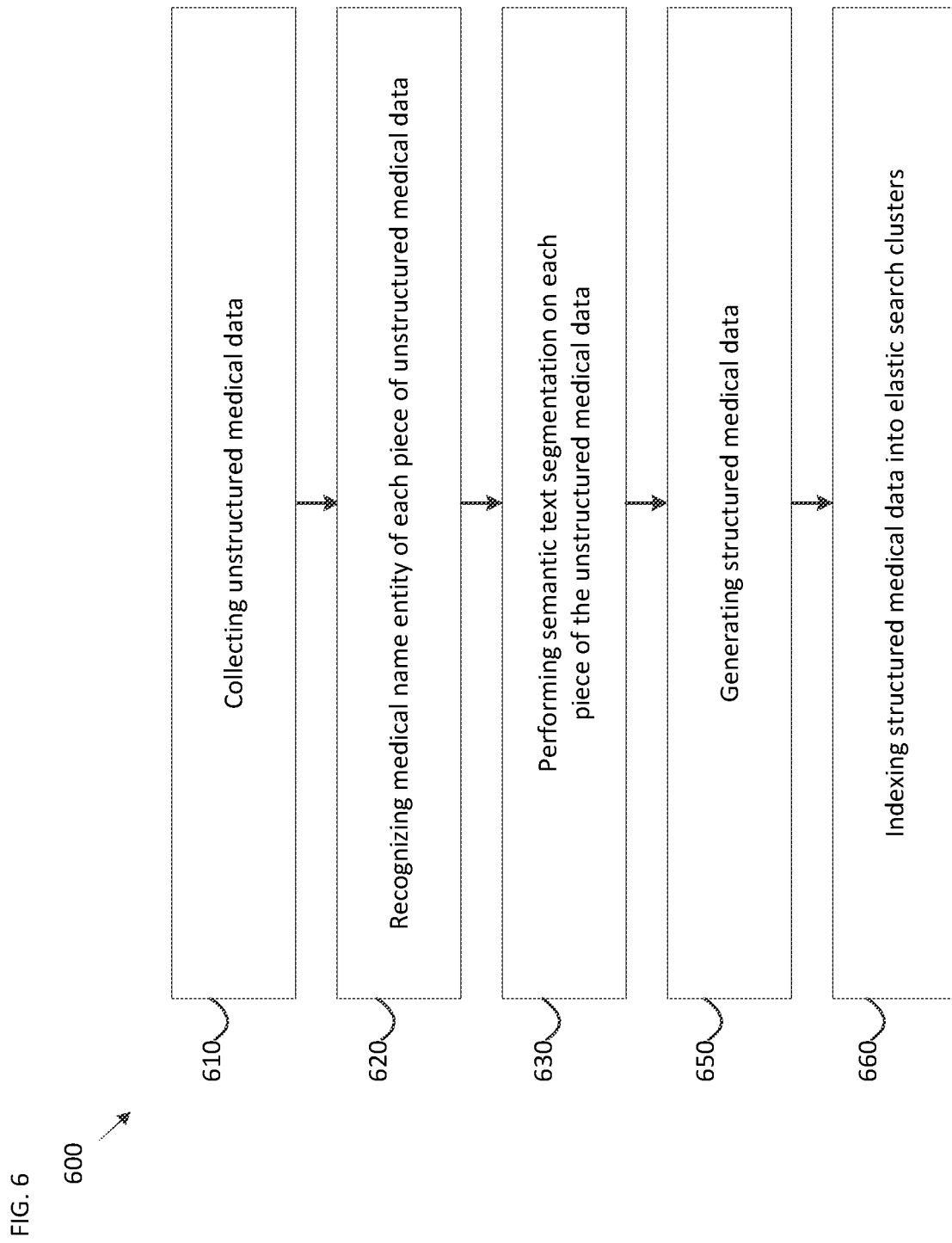
FIG. 6 is a flowchart of a method of, according to embodiments.

FIG. 6 is a flowchart of a method 600 of medical data auto collection segmentation and analysis, according to embodiments. In some implementations, one or more process blocks of FIG. 6 may be performed by the platform 120 implementing the platform 300. In some implementations, one or more process blocks of FIG. 6 may be performed by another device or a group of devices separate from or including the platform 120 implementing the platform 300, such as the user device 110.

As shown in FIG. 6, in operation 610, the method 600 includes collecting, from a plurality of sources, unstructured medical data in a plurality of formats.

In operation 620, the method 600 includes recognizing a medical name entity of each piece of the unstructured medical data, using a medical dictionary.

In operation 630, the method 600 includes performing semantic text segmentation on each piece of the unstructured medical data so that each piece of the unstructured medical data is partitioned into groups sharing a same topic.

In operation 640, the method 600 includes generating, as structured medical data, each piece of the unstructured medical data of which the medical name entity is recognized, each piece of the unstructured medical data being partitioned into the groups.

In operation 650, the method 600 includes indexing the structured medical data into elastic search clusters.

The method 600 may further include controlling to search for and display at least one of the elastic search clusters.

The method 600 may further include generating the medical dictionary, using the unstructured medical data.

The performing the semantic text segmentation may include training a latent Dirichlet allocation (LDA) model and a non-negative matrix factorization (NMF) model, using the unstructured medical data.

The performing the semantic text segmentation may further include includes, for each of sentences of the unstructured medical data outputting LDA scores and NMF scores respectively from the LDA model and the NMF model, performing a softmax function on each of the LDA scores and the NMF scores to respectively generate first standard derivation scores and second standard derivation scores, summing the first standard derivation scores and the second standard derivation scores, averaging the first standard derivation scores and the second standard derivation scores that are summed, to determine an average score, and determining a topic of a respective one of the sentences, based on the average score.

The method 600 may further include generating a hieratical tree structure of metadata of each piece of the unstructured medical data. The indexing the structured medical data may include indexing the structured medical data into the elastic search clusters, using the hieratical tree structure of metadata of each piece of the unstructured medical data.

The unstructured medical data may include any one or any combination of medical books, diagnosis cases, forum discussions and medical papers, from the Internet.

Although FIG. 6 shows example blocks of the method 600, in some implementations, the method 600 may include additional blocks, fewer blocks, different blocks, or differently arranged blocks than those depicted in FIG. 6. Additionally, or alternatively, two or more of the blocks of the method 600 may be performed in parallel.

Figure 7:
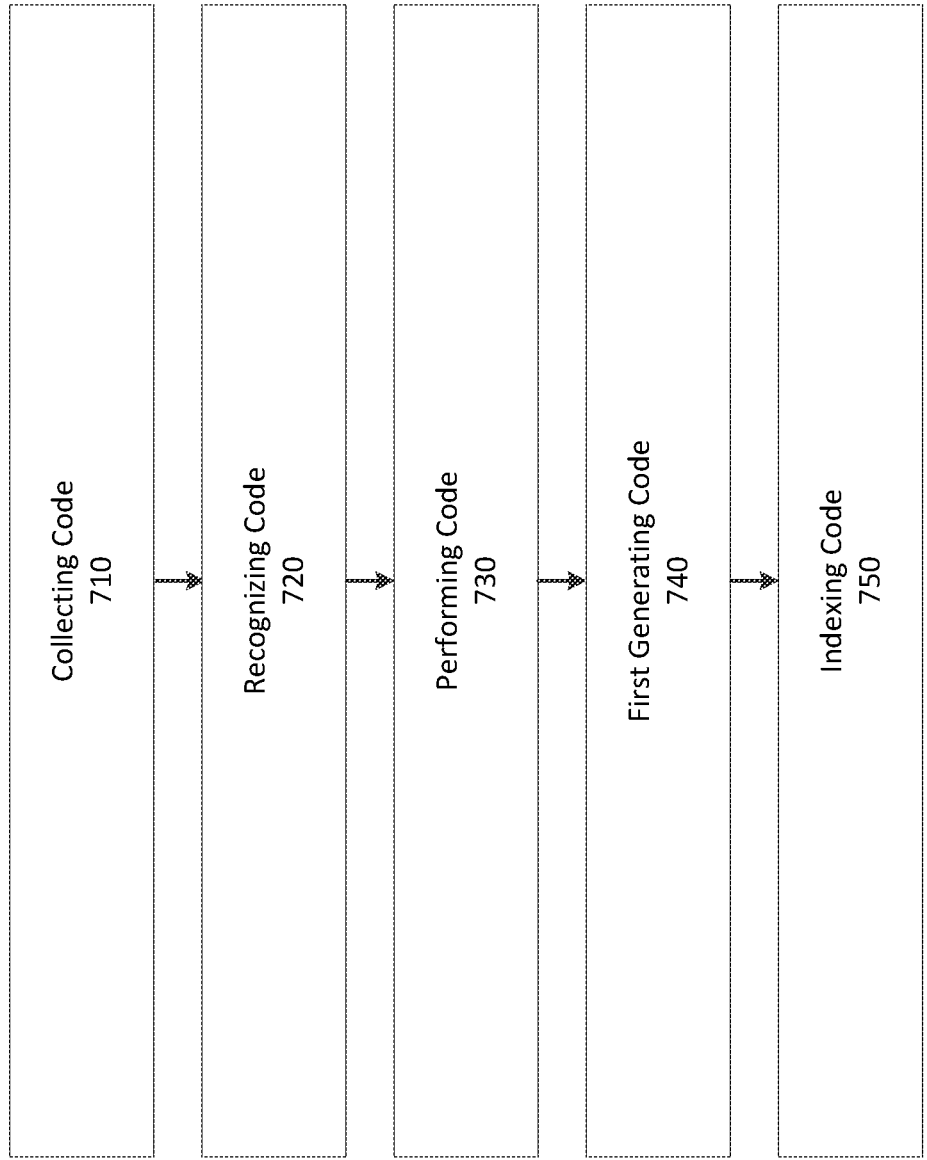
FIG. 7 is a diagram of an apparatus for, according to embodiments.

FIG. 7 is a diagram of an apparatus 700 for medical data auto collection segmentation and analysis, according to embodiments. As shown in FIG. 7, the apparatus 700 includes collecting code 710, recognizing code 720, performing code 730, first generating code 740 and indexing code 750.

The collecting code 710 is configured to cause at least one processor to collect, from a plurality of sources, unstructured medical data in a plurality of formats.

The recognizing code 720 is configured to cause the at least one processor to recognize a medical name entity of each piece of the unstructured medical data, using a medical dictionary.

The performing code 730 is configured to cause the at least one processor to perform semantic text segmentation on each piece of the unstructured medical data so that each piece of the unstructured medical data is partitioned into groups sharing a same topic.

The first generating code 740 is configured to cause the at least one processor to generate, as structured medical data, each piece of the unstructured medical data of which the medical name entity is recognized, each piece of the unstructured medical data being partitioned into the groups.

The indexing code 750 is configured to cause the at least one processor to index the structured medical data into elastic search clusters.

The apparatus 700 may further include controlling code configured to cause the at least one processor to control to search for and display at least one of the elastic search clusters.

The apparatus 700 may further include second generating code configured to cause the at least one processor to generate the medical dictionary, using the unstructured medical data.

The performing code 730 may be further configured to cause the at least one processor to train a latent Dirichlet allocation (LDA) model and a non-negative matrix factorization (NMF) model, using the unstructured medical data.

The performing code 730 may be further configured to cause the at least one processor to, for each of sentences of the unstructured medical data output LDA scores and NMF scores respectively from the LDA model and the NMF model, perform a softmax function on each of the LDA scores and the NMF scores to respectively generate first standard derivation scores and second standard derivation scores, sum the first standard derivation scores and the second standard derivation scores, average the first standard derivation scores and the second standard derivation scores that are summed, to determine an average score, and determine a topic of a respective one of the sentences, based on the average score.

The apparatus 700 may further include second generating code configured to cause the at least one processor to generate a hieratical tree structure of metadata of each piece of the unstructured medical data. The indexing code 750 may be further configured to cause the at least one processor to index the structured medical data into the elastic search clusters, using the hieratical tree structure of metadata of each piece of the unstructured medical data.

The unstructured medical data may include any one or any combination of medical books, diagnosis cases, forum discussions and medical papers, from the Internet.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, or a combination of hardware and software.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware may be designed to implement the systems and/or methods based on the description herein.

Even though combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A method of medical data auto collection segmentation and analysis, the method comprising:
   collecting, from a plurality of sources, unstructured medical data in a plurality of formats;
   recognizing a medical name entity of each piece of the unstructured medical data, using a medical dictionary;
   performing semantic text segmentation on each piece of the unstructured medical data so that each piece of the unstructured medical data is partitioned into groups sharing a same topic;
   generating, as structured medical data, each piece of the unstructured medical data of which the medical name entity is recognized, each piece of the unstructured medical data being partitioned into the groups; and
   indexing the structured medical data into elastic search clusters,
   wherein the performing the semantic text segmentation comprises:
      training a latent Dirichlet allocation (LDA) model and a non-negative matrix factorization (NMF) model, using the unstructured medical data; and
      for each of sentences of the unstructured medical data:
         outputting LDA scores and NMF scores respectively from the LDA model and the NMF model; and
         performing a softmax function on each of the LDA scores and the NMF scores to respectively generate first standard derivation scores and second standard derivation scores.

2. The method of claim 1, further comprising controlling to search for and display at least one of the elastic search clusters.

3. The method of claim 1, further comprising generating the medical dictionary, using the unstructured medical data.

4. The method of claim 1, wherein the performing the semantic text segmentation further comprises, for each of sentences of the unstructured medical data:
   summing the first standard derivation scores and the second standard derivation scores;
   averaging the first standard derivation scores and the second standard derivation scores that are summed, to determine an average score; and
   determining a topic of a respective one of the sentences, based on the average score.

5. The method of claim 1, further comprising generating a hieratical tree structure of metadata of each piece of the unstructured medical data,
   wherein the indexing the structured medical data comprises indexing the structured medical data into the elastic search clusters, using the hieratical tree structure of metadata of each piece of the unstructured medical data.

6. The method of claim 1, wherein the unstructured medical data comprises any one or any combination of medical books, diagnosis cases, forum discussions and medical papers, from the Internet.

7. An apparatus for medical data auto collection segmentation and analysis, the apparatus comprising:
   at least one memory configured to store program code; and
   at least one processor configured to read the program code and operate as instructed by the program code, the program code including:
      collecting code configured to cause the at least one processor to collect, from a plurality of sources, unstructured medical data in a plurality of formats;
      recognizing code configured to cause the at least one processor to recognize a medical name entity of each piece of the unstructured medical data, using a medical dictionary;
      performing code configured to cause the at least one processor to perform semantic text segmentation on each piece of the unstructured medical data so that each piece of the unstructured medical data is partitioned into groups sharing a same topic;
      first generating code configured to cause the at least one processor to generate, as structured medical data, each piece of the unstructured medical data of which the medical name entity is recognized, each piece of the unstructured medical data being partitioned into the groups; and
      indexing code configured to cause the at least one processor to index the structured medical data into elastic search clusters)
   wherein the performing code is further configured to cause the at least one processor to:
      train a latent Dirichlet allocation (LDA) model and a non-negative matrix factorization (NMF) model, using the unstructured medical data; and
      for each of sentences of the unstructured medical data:
         output LDA scores and NMF scores respectively from the LDA model and the NMF model; and
         performing a softmax function on each of the LDA scores and the NMF scores to respectively generate first standard derivation scores and second standard derivation scores.

8. The apparatus of claim 7, further comprising controlling code configured to cause the at least one processor to control to search for and display at least one of the elastic search clusters.

9. The apparatus of claim 7, further comprising second generating code configured to cause the at least one processor to generate the medical dictionary, using the unstructured medical data.

10. The apparatus of claim 7, wherein the performing code is further configured to cause the at least one processor to, for each of sentences of the unstructured medical data:
sum the first standard derivation scores and the second standard derivation scores;
average the first standard derivation scores and the second standard derivation scores that are summed, to determine an average score; and
determine a topic of a respective one of the sentences, based on the average score.

11. The apparatus of claim 7, further comprising second generating code configured to cause the at least one processor to generate a hieratical tree structure of metadata of each piece of the unstructured medical data,
wherein the indexing code is further configured to cause the at least one processor to index the structured medical data into the elastic search clusters, using the hieratical tree structure of metadata of each piece of the unstructured medical data.

12. The apparatus of claim 7, wherein the unstructured medical data comprises any one or any combination of medical books, diagnosis cases, forum discussions and medical papers, from the Internet.

13. A non-transitory computer-readable medium storing instructions that, when executed by at least one processor of a device, cause the at least one processor to:
collect, from a plurality of sources, unstructured medical data in a plurality of formats;
recognize a medical name entity of each piece of the unstructured medical data, using a medical dictionary;
perform semantic text segmentation on each piece of the unstructured medical data so that each piece of the unstructured medical data is partitioned into groups sharing a same topic;
generate, as structured medical data, each piece of the unstructured medical data of which the medical name entity is recognized, each piece of the unstructured medical data being partitioned into the groups; and
index the structured medical data into elastic search clusters,
wherein the instructions further cause the at least one processor to:
train a latent Dirichlet allocation (LDA) model and a non-negative matrix factorization (NMF) model, using the unstructured medical data,
for each of sentences of the unstructured medical data:
output LDA scores and NMF scores respectively from the LDA model and the NMF model; and
performing a softmax function on each of the LDA scores and the NMF scores to respectively generate first standard derivation scores and second standard derivation scores.

14. The non-transitory computer-readable medium of claim 13, wherein the instructions further cause the at least one processor to control to search for and display at least one of the elastic search clusters.

15. The non-transitory computer-readable medium of claim 13, wherein the instructions further cause the at least one processor to generate the medical dictionary, using the unstructured medical data.

16. The non-transitory computer-readable medium of claim 13, wherein the instructions further cause the at least one processor to, for each of sentences of the unstructured medical data:
sum the first standard derivation scores and the second standard derivation scores;
average the first standard derivation scores and the second standard derivation scores that are summed, to determine an average score; and
determine a topic of a respective one of the sentences, based on the average score.

17. The non-transitory computer-readable medium of claim 13, wherein the instructions further cause the at least one processor to:
generate a hieratical tree structure of metadata of each piece of the unstructured medical data; and
index the structured medical data into the elastic search clusters, using the hieratical tree structure of metadata of each piece of the unstructured medical data.

* * * * *